United States Patent
Durand

(10) Patent No.: US 7,542,912 B1
(45) Date of Patent: Jun. 2, 2009

(54) SYSTEM, APPARATUS, AND METHODS FOR DEVELOPING AND DELIVERING HEALTH INFORMATION

(76) Inventor: Whitney Durand, 1914 E. Brow Rd., Signal Mountain, TN (US) 37377

( * ) Notice: Subject to any disclaimer, the term of this patent is extended or adjusted under 35 U.S.C. 154(b) by 168 days.

(21) Appl. No.: 09/616,472

(22) Filed: Jul. 14, 2000

Related U.S. Application Data

(60) Provisional application No. 60/143,960, filed on Jul. 15, 1999.

(51) Int. Cl.
*G06Q 10/00* (2006.01)
(52) U.S. Cl. ............................... 705/2; 705/1
(58) Field of Classification Search ............. 705/2–3, 705/4, 1, 26, 400, 8
See application file for complete search history.

(56) References Cited

U.S. PATENT DOCUMENTS

| | | | |
|---|---|---|---|
| 3,566,370 A | 2/1971 | Worthington, Jr. | |
| 3,921,318 A | 11/1975 | Calavetta | |
| 5,241,466 A * | 8/1993 | Perry et al. ................. | 705/1 |
| 5,291,399 A | 3/1994 | Chaco | |
| 5,325,294 A | 6/1994 | Keene | |
| 5,499,293 A | 3/1996 | Behram | |
| 5,619,991 A | 4/1997 | Sloane | |
| 5,651,067 A | 7/1997 | Ahrens | |
| 5,651,117 A * | 7/1997 | Arbuckle ..................... | 705/4 |
| 5,659,741 A | 8/1997 | Eberhardt | |
| 5,664,109 A | 9/1997 | Johnson | |
| 5,802,876 A | 9/1998 | Miller | |
| 5,832,488 A | 11/1998 | Eberhardt | |
| 5,899,998 A | 5/1999 | McGauley | |
| 5,901,303 A | 5/1999 | Chew | |

(Continued)

FOREIGN PATENT DOCUMENTS

EP   0 837 404   4/1998

OTHER PUBLICATIONS

Standards of care: Potential implications for the counseling profession; Journal of Counseling and Development : JCD; Alexandria; Fall 1998; Paul F Granello; J Melvin Witmer; pp. 1-13.*

(Continued)

*Primary Examiner*—Matthew Gart
*Assistant Examiner*—Vanel Frenel
(74) *Attorney, Agent, or Firm*—Carr & Ferrell LLP

(57) ABSTRACT

An individual is enabled to develop medical contingency plans that are automatically activated if the individual is rendered unable to assert his or her own will by an injury or a medical condition. Medical information and health information are assembled and advance directives are formulated in a manner that combines systematic guidance to optimize contingency plan effectiveness and individual autonomy to permit individuals to design their own plan. When a participating individual is rendered unable to assert his or her own will by an injury or medical emergency, identification information and instructions carried by the individual enable responding care givers to access enforceable documents that direct medical care and address personal needs. The documents produced are designed to overcome mitigating factors associated with the urgency of the individual's condition, institutional policy, conflicting family member opinions, information transmission difficulties, the attitudes of treating physicians, language discrepancies, and the governmental rules in effect where the emergency happens.

22 Claims, 15 Drawing Sheets

U.S. PATENT DOCUMENTS

| | | | |
|---|---|---|---|
| 5,911,132 A | | 6/1999 | Sloane |
| 5,924,074 A | | 7/1999 | Evans |
| 5,974,339 A | | 10/1999 | Baker |
| 5,983,200 A | * | 11/1999 | Slotznick .................... 705/26 |
| 5,991,730 A | | 11/1999 | Lubin |
| 5,991,731 A | | 11/1999 | Colon |
| 5,993,387 A | | 11/1999 | Moore |
| 5,995,939 A | | 11/1999 | Berman |
| 5,997,476 A | | 12/1999 | Brown |
| 5,999,909 A | | 12/1999 | Rakshit |
| 6,006,191 A | | 12/1999 | DiRienzo |
| 6,021,393 A | | 2/2000 | Honda |
| 6,026,363 A | | 2/2000 | Shepard |
| 6,031,910 A | | 2/2000 | Deindl |
| 6,034,605 A | | 3/2000 | March |
| 6,055,506 A | | 4/2000 | Frasca, Jr. |
| 6,340,978 B1 | * | 1/2002 | Mindrum .................... 715/764 |
| 2002/0004757 A1 | * | 1/2002 | Torres et al. .................. 705/26 |
| 2002/0072925 A1 | * | 6/2002 | Krim ............................ 705/1 |
| 2003/0197721 A1 | * | 10/2003 | Mindrum et al. ............ 345/716 |

OTHER PUBLICATIONS

National Electronic
Lifeline Systems, Inc.
U.S. Living Will Registry
North American Registry of Living Wills.
AgeNet, LLC.
Gateway File Systems Inc.
Universal Medical History & Information, Inc.
NeoTrax, Inc.
Global Emergency Medical Services.
Mdchart, Inc.
MedicalLogic, Inc.
Telemedical.com Inc.
Drkoop.com
VitalWorks, Inc.
HealthCentral.com.
Franklin Health.
OnHealth Network Company.
HealthGate Data Corp.
AmericanDoctor.com, Inc.
Mediconsult.com, Inc.
HealthAnswers.com, Inc.
Mayo Clinic.
Healtheon/Web MD.
Ameriplast.
Centurion Technologies, Inc.
Spartanics.
e-Card.
Daniel Fisher, "Start-up City", Forbes, Oct. 19, 1998.
Advance Decisions, Interim Report.
Larry Beresford, "Improving End-Of-Life Care", Healthplan, Mar./Apr. 1999.
John T. Aquino, "Patently Permissive", ABA Journal, May 1999.
Inka Resch, "Medical Care on a Card", Business Week, Sep. 14, 1998.
John Leighty, "RealMed Thinks Smart," healthcarebusiness, Jun./Jul. 1998.
"Preventing Death and Injury from Medical Errors Requires Dramatic, System-Wide Changes", National Academy of Sciences, Nov. 29, 1999.
Draft IDS.

* cited by examiner

| ADMINISTRATIVE INFORMATION |
|---|
| 301. privacy information |
| 302. security information |
| 303. participant identification parameter |
| 304. unique identification parameter |
| 305. link to another participant |
| 306. payment account information |
| 307. customer service note |
| 308. event log information |

FIGURE 3

| END-OF-LIFE INFORMATION |
|---|
| 401. authorization to rely on a copy of an original document |
| 402. authorization to rely on a summary of an original document |
| 403. designation of at least one medication |
| 404. designation of at least one allergy |
| 405. designation of at least one health condition |
| 406. designation of at least one person to be contacted in case of emergency |
| 407. designation of at least one physician |
| 408. emergency health information |
| 409. end-of-life choice |
| 410. advance directive |
| 411. Do-Not-Resuscitate Order |
| 412. document signed by a physician concerning medical care associated with an end-of-life condition |
| 413. authorization to donate an organ |
| 414. output recipient information |
| 415. enforcement information |
| 416. medical information |
| 417. portion of an end-of-life item 401-416 |

FIGURE 4

| END-OF-LIFE CHOICE |
|---|
| 501. palliative care choice |
| 502. comfort care choice |
| 503. residence choice |
| 504. religious choice |
| 505. spiritual choice |
| 506. funereal arrangement choice |
| 507. non-medical choice |

FIGURE 5

ADVANCE DIRECTIVE 601. living will 602. medical power of attorney 603. selection of an end-of-life condition response 604. selection of medical treatment 605. refusal of medical treatment

FIGURE 6

| INFORMATION INPUT INTERFACE |
|---|
| 701. stationary telephone |
| 702. portable telephone |
| 703. cellular telephone |
| 704. mobile telephone |
| 705. the Internet |
| 706. personal computer |
| 707. facsimile machine |
| 708. smart card |
| 709. personal data assistant |
| 710. handheld computer |
| 711. computer-to-computer link |
| 712. modem |
| 713. wireless transceiver |

FIGURE 7

| INFORMATION PRODUCT |
| --- |
| 801. authorization to rely on a copy of an original document |
| 802. authorization to rely on a summary of an original document |
| 803. designation of at least one medication |
| 804. designation of at least one allergy |
| 805. designation of at least one health condition |
| 806. designation of at least one person to be contacted in case of emergency. |
| 807. designation of at least one physician |
| 808. emergency health information |
| 809. end-of-life choice |
| 810. advance directive |
| 811. Do-Not-Resuscitate Order |
| 812. document signed by a physician concerning medical care associated with an end-of-life condition |
| 813. authorization to donate an organ |
| 814. output recipient information |
| 815. enforcement information |
| 816. medical information |
| 817. summary of an information product 801-816 |
| 818. copy of an information product 801-817 |
| 819. report concerning an information set |

FIGURE 8

| INFORMATION OUTPUT INTERFACE |
|---|
| 901. stationary telephone |
| 902. portable telephone |
| 903. cellular telephone |
| 904. mobile telephone |
| 905. the Internet |
| 906. personal computer |
| 907. facsimile machine |
| 908. smart card |
| 909. personal data assistant |
| 910. handheld computer |
| 911. computer-to-computer link |
| 912. modem |
| 913. wireless transceiver |
| 914. voicemail |

FIGURE 9

|  | INFORMATION INPUT GUIDE--KEY PERSONS |
|---|---|
| 1001. | family member of said participant |
| 1002. | friend of said participant |
| 1003. | professional counselor of said participant |
| 1004. | physician |
| 1005. | lawyer |
| 1006. | spiritual adviser |

FIGURE 10

|  | INFORMATION INPUT GUIDE--KEY INSTITUTIONS |
|---|---|
| 1101. | emergency facility |
| 1102. | hospital |
| 1103. | nursing home |
| 1104. | retirement home |
| 1105. | hospice |
| 1106. | long-term care facility |
| 1107. | health care facility |

FIGURE 11

| | INFORMATION INPUT GUIDE--END-OF-LIFE CONDITION |
|---|---|
| 1201. | central nervous system disorder |
| 1202. | lung disease |
| 1203. | heart/cardiovascular disease |
| 1204. | digestive disorder |
| 1205. | kidney disease |
| 1206. | malignant disease |
| 1207. | connective tissue disease |
| 1208. | multiple organ failure |

FIGURE 12

| INFORMATION INPUT GUIDE--END-OF-LIFE CONDITION RESPONSE ||
|---|---|
| 1301. | artificial breathing sustenance |
| 1302. | artificial blood oxygenation |
| 1303. | artificial blood circulation |
| 1304. | artificial renal function |
| 1305. | radiation |
| 1306. | chemotherapy |
| 1307. | organ transplantation |
| 1308. | administration of nutrients |

FIGURE 13

|  | INFORMATION STORAGE REGISTRY FORMATS |
|---|---|
| 1401. | STANDARD |
| 1402. | NON-STANDARD |

FIGURE 14

| | REFERENCE INFORMATION INTERFACE | |
|---|---|---|
| 1501. | Electronic medical record | |
| 1502. | Guideline information | |
| 1503. | Medical protocol | |
| 1504. | Physician's practice management program | |
| 1505. | Analysis tools | |
| | 1506. | Outcome measurement |
| | 1507. | Outcome prediction |
| | 1508. | Treatment evaluation and comparison |
| | 1509. | Organ donation evaluation and comparison |
| | 1510. | Drug interaction analysis |
| | 1511. | Disease and injury correlation |
| | 1512. | End-of-life choice analysis |
| | 1513. | End-of-life information product implementation analysis |

SYSTEM, APPARATUS, AND METHODS FOR DEVELOPING AND DELIVERING HEALTH INFORMATION

This application claims the benefit of provisional application No. 60/143,960 filed Jul. 15, 1999, which is hereby incorporated by reference herein in its entirety.

BACKGROUND OF THE INVENTION

This invention relates to the assemblage, storage, and distribution of computerized medical records and advance directives. The possibility of emergencies, especially medical emergencies, is normally discussed within the family circle. Rules are set about what treatments to pursue or what to avoid, what lifestyle to lead and what behaviors to stay away from. However, having arrived at decisions on how to deal with these emergencies, implementation of a plan is often impeded because medical information and directives are dispersed and inaccessible. Also, individuals generally do not have the experience required to ensure that their decisions are able to withstand the pressures of urgency, institutional policy, conflicting family member opinions, information transmission difficulties, the attitudes of treating physicians, language discrepancies, and the governmental rules in effect where the emergency happens.

When medical information is collected and advance directives are in place, there is no guarantee that the information will be communicated to, available to, or honored by physicians. There are no requirements that doctors inquire or be informed about decisions made by participants concerning care at the end of life. Doctors may distrust a document that purports to dictate the best course to follow in the inherently complex world of medical care at the end of life. They may have found the documents they have examined previously to be too narrow or drafted for a location having different legal requirements for such documents. They may have been furnished with ambiguous or unreadable documents on prior occasions. The original document may be unavailable and they may be distrustful of copies, fearing the original may have been revoked.

Even when directives are communicated and honored, the lack of accessible and centralized medical information may contribute to errors in implementation of directives and in the provision of medical care. Medication-related errors occur frequently in hospitals and, although not all result in actual harm, those that do, are costly. The cause of many preventable errors can be traced to faulty systems.

When advance directives are duly carried out, their effectiveness is limited by the quality of the information underlying an individual's contingency planning. Although a contingency medical plan is a personal matter, it should be developed in the light of specialized knowledge that is generally inaccessible to lay persons because of the prohibitive costs associated with consulting medical specialists. There is presently no way for an individual to bring the benefit of advanced studies into his personal plan for care in anticipation of an illness or injury. Similarly, there is a need to provide individuals with the ability to make choices about emergency and end of life planning that are informed by knowledge of the best protocols available to medical personnel.

Therefore, it would be desirable to provide individuals with the ability to be fully prepared for medical emergencies and medical care at the end of their lives.

It would also be desirable to provide individuals with the ability to formulate contingency plans and advance directives that address the problems that arise due to the urgency surrounding implementation of a plan under critical conditions, institutional resistance, conflicting family member opinions, information transmission difficulties, the attitudes of treating physicians, language discrepancies, and the governmental rules in effect where the emergency happens.

Additionally, it would be desirable to provide individuals with contingency plans and advance directives that will be communicated to, available to, and honored by physicians.

It would be further desirable to provide individuals with contingency plans and advance directives that have reduced errors.

Moreover, it would be desirable to provide individuals with the ability to formulate contingency plans and advance directives that are informed by advanced medical knowledge.

SUMMARY OF THE INVENTION

Therefore, it is an object of the invention to provide individuals with the ability to be fully prepared for medical emergencies and medical care at the end of their lives.

It is also an object of the invention to provide individuals with the ability to formulate contingency plans and advance directives that are "effective." To be effective, a plan must address the problems that arise due to the urgency surrounding implementation of a plan under critical conditions, institutional resistance, conflicting family member opinions, information transmission difficulties, the attitudes of treating physicians, language discrepancies, and the governmental rules in effect where the emergency happens.

Additionally, it is an object of the invention to provide individuals with contingency plans and advance directives that will be communicated to, available to, and honored by physicians.

It is a further object of the invention to provide individuals with contingency plans and advance directives that have reduced errors.

Moreover, it is an object of the invention to provide individuals with the ability to formulate contingency plans and advance directives that are informed by advanced medical knowledge.

In accordance with the present invention systems, apparatus, and methods are provided for enabling "participants" to effect and implement choices about their medical care and contingency plans should they be rendered unable to assert their own will. A "participant" is an individual whose contingency plan or advance directive is formulated and registered according to the principles of the invention.

In one embodiment of the invention, a preferably computer-based system is provided for receiving, storing, and communicating information necessary to implement personally designed contingency plans. Each participant has control over end-of-life information that is accessibly stored in an information set in an information storage registry.

A participant inputs or designates instructions to the system for transmitting information products based on the end-of-life information stored in his information set. The participant carries identifying information that can be used, in the event of emergency, by a responding care giver to activate the system and cause information products containing health information and directives to be forwarded to designated persons.

The system includes an information input guide and a reference information interface to improve the effectiveness of the information a participant inputs, an information storage registry for storing the information, an information product producer to assemble information products from the stored information, and an information product request processor for responding to requests from care givers and dispatching information products. Additionally, the system is equipped with an information input interface and an information output interface for enabling users to utilize a wide range of telecommunication devices for exchanging information.

BRIEF DESCRIPTION OF THE DRAWINGS

The above and other objects and advantages of the invention will be apparent upon consideration of the following detailed description, taken in conjunction with the accompanying figures in which:

FIG. 3 is a partial overview of administrative information;
FIG. 4 is a partial overview of end-of-life information;
FIG. 5 is a partial overview of end-of-life choices;
FIG. 6 is a partial overview of advance directives;
FIG. 7 is a partial overview of information input interface devices;
FIG. 8 is a partial overview of information products;
FIG. 9 is a partial overview of information output interface devices;
FIG. 10 is a partial overview of key persons suggested by an information input guide;
FIG. 11 is a partial overview of key institutions suggested by an information input guide;
FIG. 12 is a partial overview of end-of-life conditions presented by an information input guide;
FIG. 13 is a partial overview of end-of-life condition responses presented by an information input guide;
FIG. 14 is a partial overview of formats used by an information storage registry;
and
FIG. 15 is a partial overview of the features on a reference information interface.

DETAILED DESCRIPTION OF THE PREFERRED EMBODIMENTS

Figure 1:
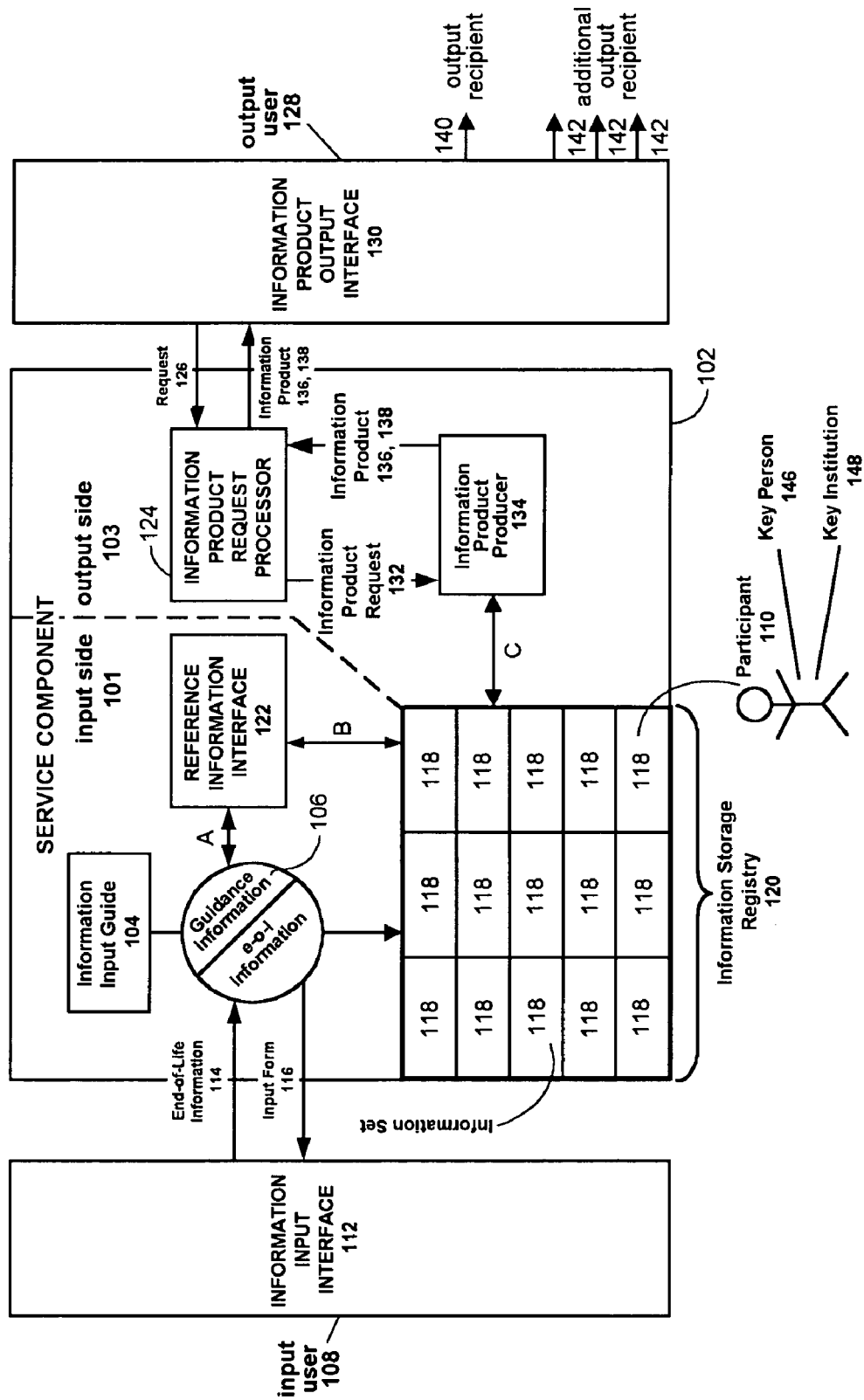
FIG. 1 is a partial overview of the invention.

The following terms as used herein have the meanings as follows:

Participant: a person using the present invention to anticipate, store, and effect choices, directives, and other orders and desires concerning their own medical, emergency, health, or other care.

Incapacitated: a condition in which a person is nonresponsive, incommunicative, or unable to act, deliberate, choose, or otherwise assert his will independently or for himself.

End of life: a situation or condition encountered by a participant while still living in which a participant is incapacitated, whether or not the participant's life is about to end.

End of life information: includes the information, choices, documents, and responses necessary to direct the care of a participant in spite of his incapacitated state.

Advance directive: a participant's selection or refusal of medical treatment in response to an incapacitating condition, a selection of a specific response to a given incapacitating condition, and documents embodying such directives such as a medical power of attorney, a living will, or other information product of the present invention.

Information product: comprises instructions and necessary supporting information to effect the advance directives or other desired response of a participant to an incapacitating condition, including replicates of raw data, such as an x-ray or a page of a medical record, provided as part of end-of-life information; copies of legal documents relating to care of the participant developed independently of the present invention and provided on behalf of the participant as part of end-of-life information (e.g., a living will prepared by the participant's personal attorney); a copy of a submittable document generated by the system in an interactive session with an input user, transmitted to the user or a key person for execution, and finally received by the service component; and additional instructions or "packaging" to accompany any of the foregoing; and a summary of any of the foregoing.

Input user: a person who may be acting for himself as a participant or as an agent of a participant that inputs end-of-life information into the system Output recipient—a person receiving an information product from the system, including the person requesting information from the system, a care giver or agent of a care-giving institution, key persons and institutions.

In a preferred embodiment, the invention is a system for providing a plurality of participants with the ability to anticipate, store, and effect choices, directives, and other orders and desires concerning their own medical, emergency, health, or other care should they be rendered unable to deliberate or act for themselves. A participant who is unable to act or deliberate for himself will herein be referred to as an unresponsive participant. It will be understood, however, that any reference to a participant who requires care according to the principles of this invention is impliedly in an unresponsive state.

The system has a service component for receiving and storing end-of-life information and producing and exporting information products in the event of an end-of-life condition.

End-of-life information includes, but is not limited to, the information necessary to direct the care of a participant in spite of his incapacitated state. The response to the occurrence of an end-of-life condition is referred to as an end-of-life condition response. An end-of-life condition response includes, but is not limited to, medical treatment.

It will be understood that "end-of-life" as used herein will not be limited to information, choices, documents, situations, conditions, and responses related to a situation in which an unresponsive participant's life is likely to end, but will also refer to those choices, documents, situations, conditions, and responses in which a participant's life may or may not be likely to end, but in which a participant lacks the ability to act, deliberate, communicate, choose, or otherwise assert his will independently or for himself. It will be further understood that even when a participant is able to act for himself, he can access the system to obtain information and information products for his convenience.

A system user, who may be acting for himself as a participant or as an agent of a participant inputs end-of-life information into the service component. End-of-life information includes copies of raw data such as scanned-in directives, forms, documents, medical images, and laboratory results. End-of-life information also includes electives issued by a user of the system. Electives include elections of information products, types of information products, or characteristics of information products that the system can produce or forward for the participant in the event of an end-of-life condition. Elections also include prospective recipients of documents and choices of conditions for triggering the transmission of the information products. Preferably, the user makes elections, via an interactive user interface. Elective documents are thus produceable, available, and transmittable in the event that an end-of-life condition arises. End-of-life information is stored in an information set corresponding to a particular participant.

Each information set preferably also includes administrative information that may include participant particulars, privacy information, billing information, security information, and privacy information.

The scope of end-of-life information is designed to anticipate the medical, ethical, legal, bureaucratic, emotional, and practical needs of participants and to ensure that any person delivering care to the participant in response to an end-of-life condition has at his disposal all the information and legal documentation necessary to effect an end-of-life condition response according to the desires of the participant despite the participant's inability to communicate or assert his will.

End-of-life information preferably further includes enforcement information to ensure enforcement of the participants wishes in any given jurisdiction or in a location in which English is not the official or primary language. Accordingly, the service component is able to produce end-of-life information products that are tailored to meet the requirements of any given prospective enforcement jurisdiction, both domestic and foreign. The service component also is able to produce information products written in non-English languages to enhance legal force in foreign countries. A user may, for example update information set 118 in anticipation of a journey.

The system preferably also includes an input interface through which a user, such as an input user, may interact with the service component. The primary function of the input interface is to convey information from an input user to the service component, but the input interface may also have output capability to facilitate the receipt of various forms of information from the input user.

The input interface allows the service component to receive information from the input user in a wide range of formats. For example, the input interface may convey a hardcopy form by conventional means, but may also convey data electronically and through wireless means.

The service component preferably includes an information product producer. The information product producer generates documents that are designed to communicate the participant's orders to a care giver in a legally binding form. The information product producer utilizes end-of-life information stored in the participant's information set to generate an information product. In one preferred embodiment, the information set is stored in a database and the information product producer has word processing functions that interact with the data base to incorporate stored data into information products suitable for output.

Information products may be replicates of raw data, such as an x-ray or a page of a medical record, stored in the information set. Raw data may be forwarded as an information product in substantially the same form in which it was input or it may be forwarded with "packaging" to make it conform to a particular information product format. Alternatively, an information product may be a computer-generated document or summary of a document. An information product may also be a copy of a submittable document generated by the service component in an interactive session with an input user, transmitted to the user or a key person for execution, and finally received by the service component. A copy of the signed document would then be stored in the information set until conditions for its transmission are fulfilled.

The invention preferably includes an output interface for enabling an output user, who may be a professional care giver or a responding lay person, to activate the invention in response to an end-of-life condition of a participant. One function of the output interface is to convey one or more information products to an output recipient. Output recipients include the output user, for example a care giver or agent of a care giving institution, and additional output recipients such as key persons and institutions. Key persons include, but are not limited to, family members, counselors, and medical personnel. Key institutions include, but are not limited to, hospitals, hospices, retirement homes, and health care management organizations. It will be understood that key persons and key institutions are preferably designated by the input user and that any person or institution designated by the input user may be considered a key person or key institution, respectively. Furthermore, references herein to key institutions will include the personnel or agents of those institutions.

The invention preferably provides the input user with the ability to designate certain key persons and institutions as output recipients to whom an information product should be transmitted in case of a specified event. The specified event may be defined in specific terms such as the arrival of a certain date or it may defined in more general terms such as the activation of the system by an output user in response to the occurrence of an end-of-life condition. The transmission of an information product to an output recipient may be done automatically and without knowledge of an output user.

The information output interface is able to convey information products to output recipients through a variety of channels and in a variety of forms. The forms include, but are not limited to, documents (which may or may not be electronic documents) and data streams (including electronic, electromagnetic, and optical data streams).

The service component also includes an information input guide. The information input guide provides information to an output user, a key person, or a key institution. Information from the information input guide is designed to educate the input user and key persons and institutions about the features of the invention, the issues that arise when a participant uses the invention, and the issues that arise when the invention is activated by an output user on behalf of an unresponsive participant. The issues are informed by knowledge of the process of effecting choices during an end-of-life condition. Information from the input information guide helps a participant make choices about end-of-life information and store end-of-life information that will most effectively and expediently compel and facilitate fulfillment of the participant's end-of-life plan.

The information input guide preferably includes a broad description of end-of-life plans in general, including suggestions of key persons and institutions that a participant may engage in the end-of-life planning process. The information input guide preferably further provides educational information and outlines of planning strategies that are appropriate for participants of different age, religion, cultural background, and family structure. The end-of-life planning information and strategies preferably further include suggestions for non-medical end-of-life information such as personal messages that a participant wishes to have delivered in the form of an information product to a key person, such as a close friend or family member, in the event that an end-of-life condition arises.

The information input guide preferably has an interactive interface for communicating with an input user. The input guide preferably allows the input user to choose forms (such as an election form indicating a set of services, information products, or end-of-life condition responses that the participant desires) and submittable documents (including, for example, executable documents such as a Do Not Resuscitate Order or an Organ Donation Authorization) that the input user, participant, or key person completes or signs and then submits to the service component via the input interface. The service component then scans the hardcopy form or document and stores it in the participant's information set, preferably in a storage registry that is discussed in greater detail below.

In particular, the information input guide provides the input user with a series of commonly encountered end-of-life conditions, such as permanent unconsciousness, and corresponding options for end-of-life condition responses, including, but not limited to, medical treatment, supplying some form of intravenous nutrition, and discontinuation of life support.

Preferably, end-of-life information, encapsulated in an information set corresponding to a given participant, is stored in an information storage registry. The information storage registry stores information in standard form, such as structured arrays or tables of end-of-life information, including elections, that are efficiently stored in a structured format. The storage registry also stores information in a non-standard format. The non-standard format provides the versatility needed to store medical images and scanned-in copies of medical records or executed documents. The storage registry also stores administrative information that is part of the information set corresponding to the participant.

End-of-life information may be stored in an electronically or electromagnetically readable format, an optically readable format, or in any other appropriate format.

Preferably, the service component also includes an interface for accessing reference information. Reference information includes, but is not limited to, guidelines for medical practice and medical protocols relevant to end-of-life conditions. Reference information may also include an electronic medical record corresponding to the participant. One guideline is a physician's practice management program. Access to reference information provides input users with information available to the medical community and helps participants make more informed decisions and guides them toward including end-of-life information that will ensure more effective care and fulfillment of their will in response to end-of-life conditions.

The reference information interface preferably also provides access to tools for analysis of end-of-life information that resides in an information set in the service component. The analysis tools, like the reference information, allow participants to make informed choices about the end-of-life information they submit to the system. The analysis tools allow an input user to obtain qualitative and quantitative information about specific medical conditions and corresponding treatments (including end-of-life condition responses) that are relevant to the participant.

Accordingly, the input user is provided with a measurement of an outcome for a given treatment or end-of-life condition response based on knowledge from medical research. Similarly, an analysis tool of the reference information interface may provide a prediction of an outcome for an end-of-life condition response. An analysis tool may also provide a comparison between the effects of different end-of-life condition responses in connection with a given end-of-life condition.

In particular, the analysis tool preferably can emphasize the importance of choosing end-of-life information prudently by illustrating the difference between the outcomes of a desired end-of-life condition response and an undesired end-of-life condition response in an unfortunate case where an individual did not have the benefit of an effective end-of-life planning system. Treatment comparison has special relevance to choices about acceptance of organ donation.

Additionally, the reference information interface analysis tools preferably provide the input user with current information about drug interactions, and interrelationships between different diseases and injuries to help the participant improve the quality and relevance of the end-of-life information that is submitted to the invention.

The reference information interface preferably also serves the medical research community by permitting analysis of end-of-life information contained in information sets corresponding to participants. In particular, the medical research community may be provided with statistics about the choices that individuals make, the importance of responding to the desires of those individuals, and information that can help care givers learn how to better serve the needs of individuals who have developed an end-of-life plan. It will be appreciated that external analysis of end-of-life information may be conducted via channels other than the reference information interface. For example, an authorized researcher may be provided access to end-of-life information by a specialized research interface or module.

It will be understood that the reference information interface and associated interface for analysis tools anticipate the continued development of new reference information and analysis tools. The invention contemplates providing access to new information and analysis tools as they become available.

Preferably, the invention also includes an information product request processor. The information product request processor receives requests, via the information output interface from an output user. A participant is preferably provided with an identification instrument which may be in the form of an identification card or a smart card. If an end-of-life condition arises, an individual who comes to the aid of the unresponsive participant, provides care or treatment to the unresponsive participant, or is involved in responding to the end-of-life condition, is instructed by the identification instrument to access the output information interface. The identification instrument provides identification information and security information that the attending individual can use to access and obtain the information products generated in accordance with the end-of-life information and the end-of-life plan chosen by the participant.

Preferably, in response to activation of the system by an output user, information products may be transmitted to any output recipient previously specified by an input user, to the output user himself, or to output recipients that the output user may designate. Additionally, if the participant has not done so already, the output user may designate a particular language or jurisdiction relevant to the geographic location in which an end-of-life condition response is to be implemented for the non-responsive unresponsive participant. Translations of summaries and of portions of information products based on standard end-of-life information may be produced by the use of translation software, by a human translator, by a combination thereof, or by any other means. Since non-standard information may be entered into the information storage registry, imaged copies of documents of any kind and in any language may be stored for later transmission.

In another preferred embodiment the invention is provided as an apparatus for providing participants with the ability to effect choices about their care should they become unresponsive. The apparatus includes memory equipment for storing at least one information set corresponding to each participant and data processing equipment for performing the functions of information input guide, reference information interface, information product producer, and information product request processor.

The apparatus preferably also includes input equipment for allowing an input user corresponding to a given participant to input end-of-life information (both raw data and elections). Additionally, the apparatus preferably includes output equipment for enabling an output user to request an information product that is produced from the end-of-life information contained in the participant's information set.

The following hypothetical illustration demonstrates some of the features of the invention. The illustration concerns a 53-year old woman and her 81-year old widowed mother (participant) residing in the United States.

The participant's medical records were scattered among a number of primary care physicians, medical specialists, hospitals, and laboratories because she had lived in several different localities. Over the years, the participant acquired indemnity insurance, Medicare HMO coverage, and, later, regular Medicare benefits. The participant had emphysema in its early or middle stages.

The participant's mental condition was excellent and she desired to not become a burden to her children at any time preceding her death. The participant indicated that she wished to discuss end-of-life information products with key persons such as her physician, a lawyer, and her daughter. She also planned to visit her son in Austria, a prospective enforcement jurisdiction. Her daughter agreed to go with her and to assist her mother with end-of-life planning and other preliminary arrangements regarding health as well as travel. These arrangements would be completed by using the present invention.

During the course of her visit to Austria, the participant experienced an end-of-life condition. The participant stopped breathing, suffered brain damage, fell into a coma, was placed on life support (an undesired end-of-life condition response), and died in the presence of two of her children after life support was removed. The removal of life support was a desired end-of-life condition response corresponding to an end-of-life choice that she had chosen and registered according to the principles of the invention. The desired end-of-life condition response was attained only through overcoming the resistance of attending care givers using this invention.

Using this invention the participant and her daughter acted as follows before and during the participant's trip:

Initial Search for Information

At the participants' request, the daughter made a search of the Internet and found a web site that used this invention. The invention provided the daughter provided with the following resources: (1) explanations about medical care in emergencies, especially those occurring while traveling, and at the end of life (information input guide), (2) the ability to prepare drafts of health care documents online so that her mother can sign them after discussing them with her doctor and a lawyer (information input guide), and (3) information storage registry for the documents that her mother signed so that they would be available at all times and in all places (service component functions, as described above).

In this illustration, the daughter did not complete a worksheet at the web site so as to prepare and print documents, but instead downloaded the worksheet in order for her mother to make decisions later.

Compilation of Emergency Health Information (A Category of End-of-Life Information)

The needed emergency information consisted of important medical conditions such as emphysema, prescriptions, insurance coverage, and the names and telephone numbers of key persons who would also become output recipients, such as doctors and other persons to contact. The participant and her daughter were able to compile the information and list it on the worksheet that the daughter had downloaded from the Internet for later entry and storage of information in the information storage registry.

Compilation of Other Health Information

The participant caused non-emergency information to be transmitted to the registry before her trip to Austria. Her physician's x-ray identifying her condition of emphysema was transmitted to the registry so that it could be stored there.

Storage of Emergency Health Information in the Registry

The daughter made a second visit to the Internet, this time to enter emergency health information concerning the participant. A written statement of that information was produced by the service component for verification. The daughter was advised that a signature on the document would be accepted but was not required for storage of emergency health information in the database. The daughter printed a letter-sized sheet containing an identification instrument. Identification instruments include, but are not limited to, wallet-sized printouts, plastic cards, and smartcards. The identification instrument showed the participant's name, gender, Social Security Number, personal identification number, a toll-free number for obtaining the information stored in the database, and the Internet address of the registry. The daughter was also advised that the same information would be contained on a plastic card of the same size that would be sent later to her mother. Finally, the daughter was told that the entirety of the emergency health information would be placed on her mother's personal data assistant or smart card if she had one that was compatible with the registry's software and if there was sufficient storage space remaining on it.

Storage of Other Health Information in the Registry

In this illustration, other health information was transmitted by a doctor's office to the service component by automated interface over telephone lines. Minimal effort was required on the part of the doctor's staff. The staff was required to keypunch only the participant's name, gender, Social Security number, personal identification number, and the identification of the type (lab analysis, x-ray, and so forth) and the date of the record. If the doctor's office had had the necessary equipment and the participant a smart card, the only keypunching would have been of the type and date of the record.

Testing Emergency Health Information for Medical Errors

Using the reference information interface and associated analysis tools, the service component tested medical conditions and prescriptions for medical complications and errors. If it found that participant was taking a prescription for one condition that aggravated another, or that was incompatible with another prescription, an alert would have been sent to the participant and her doctor. In the this case, no possibly adverse drug reaction was found.

Discussions about End-of-Life Medical Care

Pamphlets concerning end-of-life planning were downloaded from the web site and formed a basis for discussions among participant, daughter, doctor, and lawyer. The doctor advised that a Do-Not-Resuscitate Order was inappropriate because the participant's emphysema was serious but not grave. The participant decided that she wanted to make a donation of her corneas, which were in good condition, and to authorize her daughter to make medical decisions for her, including the withdrawal of life support, should she become incapacitated.

Independent Legal Advice about Use of Advance Directives

The participant discussed the alternatives available in signing advance directives with a lawyer located by her daughter, and decided to use a health care power of attorney and organ donation form associated with this invention, rather than the documents available from other sources. The service component of this invention can accommodate images of documents from other sources but the participant chose to use comprehensive documents generated by the information product producer of this invention because they can be transmitted in summary form. Summaries are more likely to be read by a physician under the stress of caring for a participant experiencing an end-of-life condition.

Preparation of Advance Directives

During the daughter's third visit to the Internet, she made elections that the participant had made concerning end-of-life condition responses and donation of her corneas. The daughter then printed the relevant documents. A health care power of attorney stated that the daughter was authorized to determine when, but not whether, life support of any type must be refused or discontinued should the participant be in the final stages of any form of terminal condition, including permanent unconsciousness. The documents were then signed in the presence of witnesses and sent to the service component for scanning and indexing.

Transmission of Emergency Health Information and Summaries of Documents when Needed The participant traveled to Austria and both the emergency health information and summaries of the health care power of attorney and organ donation were needed when the participant's end-of-life condition occurred. The participant stopped breathing and suffered brain damage. The most convenient method of access to the service component was the Internet, rather telephone, followed by a fax. Emergency personnel at a hospital in Salzburg, Austria became output users and output recipients. Having German as a primary language, they requested online that information products be transmitted with German as the information product language.

Transmission of Other Health Information

The x-ray was available as non-emergency end-of-life information and was transmitted over telephone lines to the Salzburg hospital's computer where it could be read. In view of the damage to the participant's brain, the x-ray's chief value was to confirm that her lungs were so weak that she would need permanent connection to a ventilator.

Implementation of the Participant's Instructions Concerning Medical Care at the End of Life The information products (viz., summaries of the health care power of attorney and the organ donation form) were specific about the life-prolonging treatment to be administered to the participant and her gift of corneas. They were in the primary language, German, spoken by the doctors and hospital staff. Nevertheless, it took time and persuasion to accomplish the participant's objectives.

The health care power of attorney gave the daughter alone authority to act for the participant, but the participant's son living in Austria and another child residing in the United States were irritated about their lack of decision-making power. To overcome the familial resistance, it was necessary to produce additional information products—namely, images of the documents bearing the participant's signature (residing in the participant's information set as end-of-life information) as well as the summaries of them produced by the information product producer. Both documents stated that summaries and images had the same effect as the originals.

Nevertheless, the daughter, as an authorized output user, requested and received from the service component registry fax transmission of images of the two documents signed by her mother, the participant.

The daughter also requested and received from the information product request processor full-text translations of the health care power of attorney and corresponding summary because the daughter anticipated that the hospital's administration and attorneys would demand them in addition to the summaries in German. Ultimately, Austrian lawyers concluded that Austrian courts would recognize such documents signed in the U.S. by an American in spite of a prevalent cultural prejudice against advance directives in Austria.

In this illustration the invention overcame bureaucratic, cultural and familial resistance to the use of advance directives. The information products produced by the invention effected an acceptance of the participant's desire to have life support systems withdrawn.

The Organ Donation

Several European countries presume that all usable organs are intended to be donated unless the participant has made a written statement to the contrary. National and European registries are maintained so that objections can be stated and accessed. The participant's written refusal to donate other organs, and its placement in the storage registry associated with this invention, asserted her lawful objection to donate other organs, but enabled the donation of the corneas.

Benefits for Medicine

The daughter was aware that the registry accepted information about what actually happened to participants in emergencies and at the end of life so that outcomes could be measured, predictive models developed, and medical protocols refined. She, therefore, returned to the Internet and answered questions posed by researchers to assist in developing better medical practices.

Preferred embodiments of the invention will now be described with reference to the figures.

FIG. 1 shows an overview of system 100 of the invention. The invention centers around service component 102. Information input guide 104 on input side 101 of service component 102 provides guidance information 106 to input user 108. Input user 108 may be the same person as participant 110 or may be an authorized or appointed agent of participant 110. Input user 108 accesses service component 102 by logging on to system 100 through information input interface 112. Input user 108 transmits end-of-life information 114 to service component 102 via information interface 112. Information input guide 104 may supply input user 108 with input form 116 for subsequent submission to service component 102. Input form 116 may be an executable document scripted by service component 102. Alternatively, input form 116 may be an election worksheet for user 108 to indicate end-of-life information elections. End-of-life information 114 is then stored in information set 118 in information storage registry 120. Information storage registry 120 contains a plurality of information sets 118, each corresponding to a participant such as participant 110.

Reference information interface 122 provides reference information and access to analysis tools to input user 108 (arrow A) to assist input user 108 in making decisions regarding end-of-life planning that are informed by current medical knowledge. Reference information interface 122 also may provide medical researchers with access to end-of-life information in participant information sets (arrow B) to assist in medical research in the area of end-of-life condition response and treatment.

Output side 103 of service component 102 features information product request processor 124 for receiving requests 126 from output user 128 via information output interface 130. Output user 128 responds to an end-of-life condition in participant 110 by logging on to system 100 through information output interface 130 and issues a request to information product request processor 124 for one or more information products. Information request processor 124 issues information product request 132 to information product producer 134. Information product producer 134 accesses information set 118 (arrow C) corresponding to participant 110. (Output user 128 supplies participant identification information furnished by an identification instrument preferably carried by participant 110.)

Figure 2:
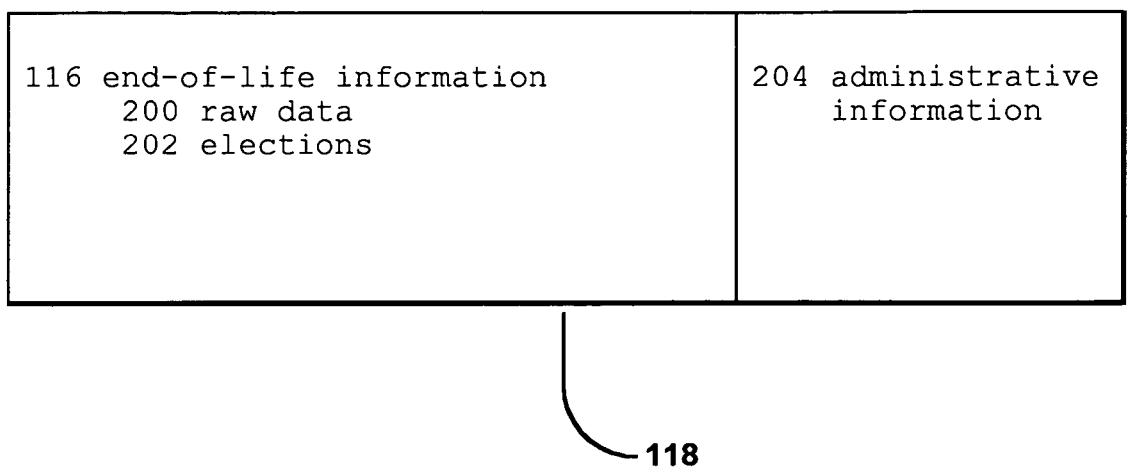
FIG. 2 is a partial overview of an information set.

End-of-life information 116, stored in information storage registry 120, includes both raw data 200 and end-of-life elections 202 (see FIG. 2). Information product producer 134 can capture raw data 200 for transmission to output recipient 140 as information product 136. Output recipient 140 will in most cases be identical to output user 128, but also may be a key person 146 or a member of a key institution 148.

Alternatively or additionally, information product producer 134 utilizes an election 202 to produce an information product 138 that is a standardized document (such as a form or a form letter) or a summary of a document. Information products 136 and 138 are preferably used in conjunction with each other to effect the choices of participant 110 through the actions of output user 128.

Service component 102 preferably also directs information products 136 and 138 to additional output recipient 142. The transmission of information products 136 and 138 to additional output recipient 142 may be predetermined by a request of participant 110 in accordance with end-of-life information 116.

FIG. 2 shows the basic contents of information set 118. Information set 118 includes both end-of-life information 116 and administrative information 204. End-of-life information includes raw data 200. Raw data 200 include any image, such as a medical image, or document, such as a laboratory report or legal document, that is stored as an image. Raw data 200 are preferably scanned-in or received electronically. Elections 202 are designations of choices made by input user 108. Examples of elections are choices to issue a Do Not Resuscitate Order or a choice of a particular end-of-life condition response to a particular end-of-life condition, as will be discussed in more detail below.

FIG. 3 shows a basic set of administrative information 204. Privacy information 301 includes records necessary to assure the privacy of a participant and his choices. Security information 302, participant identification parameter 303, and unique identification parameter 304 include information necessary to assure that the system is secure from intrusion and allows participants, authorized key persons, input users, and output users to gain access to information within bounds set by the system administration and participant 110.

Link to another participant 305 preferably records links to another participant that is a family member of participant 110. Link to another participant 305 can also link participants pairs wherein one participant appears as a key person in the other participant's information set. Payment account information 306, customer service note 307, and event log information 308 keep track of the billing records of participant 110, interactions between customer service personnel and participant 110, and any input user 108 activity, output user 128 activity, or information products 136 or 138 transmissions connected with information set 118 corresponding to participant 110.

FIG. 4 shows types of end-of-life information 114 that input user 108 can input through information input interface 112. Authorizations 401 and 402 authorize a care giver responding to an end-of-life condition in participant 110 to act on a copy or a summary, respectively, of an original document. The care giver is thus given permission to act in response to information products 136 or 138 which preferably include copies or summaries of original executed documents. End-of-life information 403-405 includes designations of medications, allergies, or other health conditions related to participant 110 that could be relevant in choosing or administering an end-of-life condition response for participant 110.

End-of-life information 406 and end-of-life information 407 are designations of key persons, 407 referring to a medical professional to be contacted in the event of an emergency or end-of-life condition. Emergency health information 408 includes, but is not limited to, important medical conditions such as emphysema, prescriptions taken, insurance coverage, and the names and telephone numbers of doctors and other key persons to contact if an end-of-life condition arises.

End-of-life choice 409 is shown in more detail in FIG. 5. End-of-life choice 409 includes, but is not limited to, a palliative care choice 501 (the type, extent, and setting of symptom-relieving care when there is no hope for a cure), a comfort care choice 502 (the manner of and extent to which an unresponsive participant is maintained in comfort, preferably regardless of the chances for a cure), and a residence choice 503 (specifying where and in what manner participant 110 should reside if long-term care is needed). End-of-life choice 409 may also be religious 504 or spiritual 505 choice to assure that care will be consonant with the religious or spiritual desires of participant 110. Likewise, end-of-life choice 409 may be a funereal or burial choice designating a type of funereal process such as burial, a location for burial, or specifying burial expenses. Non-medical end-of-life choice 507 includes personal statements or directives to family, friends, or others.

Advance directive 410 is detailed in FIG. 6. One type of advance directive 410 is living will 601. A living will is a commandment by participant 110 to a key person 146 or another person to stop medical care when participant 110 is in a specified end-of-life condition. The commandment of living will 601 gives key person 146 or another person to whom the commandment is directed an obligation to carry out the will of participant 110. The commandment leaves no discretion in the hands of the commanded person.

Medical power of attorney 602 (alternatively known as a health care power of attorney) confers discretion over the end-of-life care of participant 110 to a key person and authorizes many forms of end-of-life condition response when participant 110 is in an end-of-life condition. Medical power of attorney 602 can permit or require a key person 146 of participant 110 to terminate medical care when participant 110 is in a specified end-of-life condition.

Advance directive 410 may include a specific selection of an end-of-life condition response 603. (Some specific end-of-life conditions and end-of-life condition responses are shown in FIGS. 12 and 13, respectively.) More generally, advance directive 410 may include a selection of any medical treatment 604 or a refusal of any medical treatment 605.

Do-not-resuscitate order 411 is a specialized form of advance directive that is signed by a physician of participant 110 and directs that certain life-prolonging treatments, usually including but not limited to, cardiopulmonary resuscitation, not be administered.

End-of-life information 412 includes any document signed by a physician of participant 110 concerning medical care associated with an end-of-life condition. Document 412 includes physician-signed documents that do not fit into the aforementioned categories.

Authorization to donate an organ 413 may be relevant in both emergent and non-emergent situations. Authorization 413 is a structured directive, tailored to the needs of participant 110, to provide detailed instructions for the harvesting of organs. Authorization 413 preferably also includes the granting of authority to key persons 146 to participate in the decisions about whether or not an organ should be donated.

Output recipient information 414 assures the proper linkages between information products 136 or 138 and output recipients 142 and additional output recipients 144 (preferably including key persons 146 and key institutions 148). Output recipient information 414 identifies and includes contact information and primary language designation for output recipient 140 and additional output recipients 142. Output recipient information 414 also preferably includes conditions, defined by participant 110, upon the fulfillment of which a given information product 136 or 138 is to be transmitted to a given output recipient 140 or additional output recipient 142.

The ability to determine the contents of information products 136 and 138, the output recipients 140 and additional output recipients 142 of information products 136 and 138, and the conditions required for those transmissions to occur gives participant 110 full control over the use of the invention and the end-of-life information in his information set 118 in storage registry 120.

Enforcement information 415 preferably includes designations of prospective enforcement jurisdictions. A prospective enforcement jurisdiction is a locality, either domestic or foreign, which participant 110 foresees entering. A prospective enforcement jurisdiction may require special documentation or recognize only a specialized version of an information product relevant for end-of-life conditions (for example, the required number of witnesses on certain advance directives varies from state to state in the United States). The invention associates a prospective enforcement jurisdiction with a corresponding enforcement parameter that is applied to each information product 136 or 138. The enforcement parameter assures that the jurisdictional requisites are met for end-of-life information in information set 118 and in information products 136 and 138. A primary prospective enforcement jurisdiction may be designated either by input user 108 or an output user 128.

It will be understood that while the invention is capable of generating information products that are customized for a particular jurisdiction, it contemplates the enforcement of information products in all jurisdictions that recognize such information products. Furthermore, an information product that is tailored to a particular jurisdiction substantially fulfills the enforcement requirements of all jurisdictions that recognize such an information product.

Enforcement information 415 preferably also includes a designation of a primary language corresponding to a primary prospective enforcement jurisdiction or to a specifically anticipated output user 128 or output recipient 140 or 142. Accordingly, information product producer 134 produces information products 136 and 138 having an information product language that corresponds to the designated primary language. A primary language may be designated by input user 108 or output user 128. Additional information product languages may be specified and linked to particular anticipated output recipients 140 or 142.

Medical information 416 includes end-of-life information that may be relevant to either emergent or non-emergent end-of-life conditions. Medical information 416 generally refers to information generated by medical treatment or analysis of participant 110 prior to activation of the invention in response to an end-of-life condition. Medical information 416 may include, but is not limited to, a medical record, a laboratory report, a medical image, or a portion of the same. Similarly, a portion 417 of any end-of-life information items 401-416 may be stored in information set 118 in storage registry 120 when it is necessary for the sake of convenience or efficiency.

Portion 417 refers to an end-of-life information item that is not completely entered in information storage registry 120.

FIG. 7 shows the elements 701-713 of information interface 112. Input user 108 can transmit end-of-life information to service component 102 via any telecommunication device.

FIG. 8 shows information products 136 and 138. As discussed above, information products (such as 136) may incorporate raw data 200 or may be substantially created or assembled by information product producer 134 using elections 202 (forming an information product such as 138). In general, types of information products 136 and 138 correspond to their corresponding end-of-life information sources. Accordingly, the types of information products shown in FIG. 8 substantially correspond to the end-of-life information products shown in FIGS. 4-6 and described above. Information products include, but are not limited to, documents. Report 819 is a report concerning an information set and may be used to poll administrative information 204 for official use or may be used to provide output user 128 with an overview of the available information products for participant 110.

FIG. 9 shows information output interface 130 devices and is similar to information input interface 112 devices shown in FIG. 7.

FIGS. 9 and 10 lists key persons and key institutions, respectively, that information input guide 104 preferably suggests be involved in the end-of-life planning process of participant 110. Key persons and key institutions may also be designated as output recipient 140 or additional output recipients 142.

FIG. 12 shows 8 broad categories of end-of-life conditions that information input guide 104 preferably presents to input user 108 for possible choice, as an election 202, for directing a corresponding end-of-life condition response. Central nervous system disorder 1201 includes, but is not limited to, massive stroke, spinal cord injury or stroke causing permanent paralysis of limbs, progressive brain disease or injury such as Alzheimer's disease, severe progressive Parkinson's disease, and progressive degeneration of the nervous system such as Lou Gehrig's disease. Lung disease 1202 includes, but is not limited to, severe emphysema and chronic lung scarring. Heart/cardiovascular disease 1203 includes, but is not limited to, chronic heart failure (unresponsive to drug therapy), massive heart attack, and chronic heart muscle disease. Digestive disorder 1204 includes, but is not limited to, loss of extensive bowel from circulation failure, inflammatory disease or surgery, and progressive liver failure. Kidney disease 1205 includes, but is not limited to, chronic failure requiring a kidney machine to sustain life and severe acute kidney injury. Malignant disease 1206 includes, but is not limited to, cancers inoperable or untreatable by accepted medical guidelines, cancers spreading from one part of the body to other parts with no response to therapy, and associated consequences of a cancer causing progressive failure of the central nervous system. Connective tissue disease 1207 includes, but is not limited to, lupus and other diseases which affect skin or muscle and become severe and progressive in their final stages. Multiple organ failure 1208 may be caused, inter alia, by accidental injury or overwhelming infection.

It will be understood that the end-of-life conditions listed here are not the only end-of-life conditions that can be addressed by the invention. Advance directives aimed at end-of-life conditions of any type and scope may be specified by input user 108 because the invention is not limited to, the input, storage, and output of structured data and because participant 110 has control of the contents of information set 118.

FIG. 13 shows end-of-life condition responses that participant 110 may elect as part of an advance directive in the event of an end-of-life condition such as one of those listed above. Artificial breathing 1301, blood oxygenation 1302, blood circulation 1303, and renal functions preferably involve using devices to take the place of respiratory, cardiac, and kidney functions, respectively. Radiation 1305 and chemotherapy 1306 preferably are employed to alleviate pain, contain, or cure malignant diseases. Organ transplantation 1307 preferably includes, but is not limited to, replacement of the heart, lungs, pancreas, gastrointestinal tract, kidney, or liver. Administration of nutrients 1308 preferably involves the provision of tubes to supply food, water, and medications to the body when the gastrointestinal tract is not functioning.

FIG. 14 shows the two basic information storage registry formats. Standard information 1401 includes, but is not limited to, election 202. This may include, for example, selections of end-of-life condition responses to be included in an advance directive and responses to forms asking input user 108 for information such as emergency health information 408 or output recipient information 414.

Non-standard information 1402 preferably includes, but is not limited to, medical images such as x-rays and electronic copies of signed documents, such as a do-not-resuscitate order.

FIG. 15 shows the features of reference information interface 122. Reference information interface 122 preferably is an interface to an online reference source or an interface to an intrinsic resource such as a file server or database. Reference information interface 122 provides input user 108 with comparative information and analysis tools to make informed decisions about which types of end-of-life information 114 to register in an information set 118. Reference information may include, but is not limited to: an electronic medical record 1501 corresponding to participant 110; guideline information 1502, medical protocol 1503, and physician's practice management program 1504, which are resources from the medical profession that report the best techniques available for treating prevalent medical conditions; and analysis tools 1505.

Analysis tools 1505 preferably allow input user 108 to obtain quantitative measures of outcomes for individuals with similar medical histories who experience a given end-of-life condition (outcome measurement 1506 and outcome prediction 1507). Treatment evaluation and comparison 1508 and organ donation evaluation and comparison 1509 allow comparisons of outcomes, merits, and risks between specific treatments for a given end-of-life condition. Drug interaction analysis 1510 alerts input user 108 to existing drug interaction dangers (assuming that medication information 403 is part of the information set 118 of participant 110) and the potential danger based on any drug that might be administered in the course of an end-of-life condition response.

Disease and injury correlation analysis tool 1511 helps input user 108 anticipate end-of-life planning needs and possible end-of-life conditions.

End-of-life choice analysis 1512 and end-of-life information product implementation analysis 1513 provide information about participants' choices and experiences with end-of-life planning and actual responses to end-of-life conditions to the medical community (for research and practice). End-of-life choice analysis 1512 and end-of-life information product implementation analysis 1513 preferably help educate the medical community and care givers about end-of-life planning and thus improve the effectiveness of end-of-life planning for participants.

What is claimed is:

1. A method of providing a plurality of participants with an ability to effect choices about future care of said participants, said method comprising:

receiving from an input user, via an interactive user interface accessible through an internet connection, raw data relevant to the future care of a participant should said participant prior to death become incapacitated;

providing via said interface guidance information comprising at least one input form, said at least one input form comprising electives available to said participant regarding said future care, and reference information associated with said available electives;

analyzing said available electives in response to input by said input user to provide via said interface analysis information regarding said future care to allow informed choices of said electives to be made;

receiving from said input user via said interface at least one election of at least one of said electives;

providing said input user an identification instrument comprising a unique identification parameter corresponding to said participant;

storing in a computer-readable registry end-of-life information and said unique identification parameter in a form of an information set corresponding to said participant, said end-of-life information comprising said received raw data and said at least one election;

receiving a request from an output user identifying an occurrence of an incapacitated state in said participant;

verifying that said request includes said unique identification parameter;

if so, generating an information product derivative of said information set comprising said participant's election corresponding to said incapacitated state, said information product being generated in a form that is enforceable in a jurisdiction from which said request was received; and communicating said information product to an output recipient.

2. The method of claim 1, wherein said analysis information is selected from the group consisting of:

a. a measurement of an outcome for at least one of said participant's choices regarding care;

b. a prediction of an outcome for at least one of said participant's choices regarding care;

c. a comparison of alternative choices regarding said participant's care; and d. interaction of drugs identified by participant in said end-of-life information.

3. The method of claim 1, wherein said first providing step further comprises providing a second input form to said user for subsequent submission.

4. The method of claim 3 wherein said second input form is selected from a group consisting of an executable document and an election form.

5. The method of claim 1, wherein said end-of-life information is selected from a group consisting of:

a. an authorization to rely on a copy of an original document;
b. an authorization to rely on a summary of an original document;
c. a designation of at least one medication;
d. a designation of at least one allergy;
e. a designation of at least one health condition;
f. a designation of at least one person to be contacted in case of emergency;
g. a designation of at least one physician;
h. emergency health information;
i. an end-of-life choice;
j. an advance directive;
k. a Do-Not-Resuscitate Order;
l. a document signed by a physician concerning medical care associated with an end-of-life condition;
m. an authorization to donate an organ;
n. output recipient information;
o. enforcement information;
p. medical information; and
q. a portion of an item selected from the group a through p, above.

6. The method of claim 5 wherein when said end-of-life information is an end-of-life choice, said end-of-life choice is a choice selected from the group consisting of:
   a. a palliative care choice;
   b. a comfort care choice;
   c. a residence choice;
   d. a religious choice; and
   e. a spiritual choice.

7. The method of claim 5 wherein when said end-of-life information is an advance directive, said advance directive is an advance directive selected from the group consisting of:
   a. a living will;
   b. a medical power of attorney;
   c. a selection of an end-of-life condition response;
   d. a selection of medical treatment; and
   e. a refusal of medical treatment.

8. The method of claim 1, wherein said guidance information comprises:
   a designation of at least one end-of-life condition; and
   a designation of at least one end-of-life condition response, wherein said input user can choose at least one of said at least one end-of-life response for response to at least one of said at least one end-of-life condition.

9. The method of claim 1, wherein said information product is selected from a group consisting of:
   a. an authorization to rely on a copy of an original document;
   b. an authorization to rely on a summary of an original document;
   c. a designation of at least one medication;
   d. a designation of at least one allergy;
   e. a designation of at least one health condition;
   f. a designation of at least one person to be contacted in case of emergency;
   g. a designation of at least one physician;
   h. emergency health information;
   i. an end-of-life choice;
   j. an advance directive;
   k. a Do-Not-Resuscitate Order;
   l. a document signed by a physician concerning medical care associated with an end-of-life condition;
   m. an authorization to donate an organ;
   n. output recipient information;
   o. enforcement information;
   p. medical information;
   q. a summary of an information product selected from the group consisting of a through p, above;
   r. a copy of an information product selected from the group consisting of a through q, above; and
   s. a report concerning said end-of-life information.

10. The method of claim 1, wherein said information set comprises said end-of-life information stored in a standardized form.

11. The method of claim 10, wherein said generating step comprises translating said information set into an information product in a language other than that native to said input user.

12. The method of claim 10, wherein said generating step comprises generating an information product legally enforceable in a jurisdiction other than that in which said participant resides.

13. A method of providing a participant with an ability to effect choices about future care of said participant should said participant prior to death become incapacitated, said method comprising:
   providing via an interactive user interface accessible through an internet connection guidance information comprising at least one input form, said at least one input form comprising electives available to said participant regarding said future care, and reference information associated with said available electives;
   analyzing said available electives in response to input by said input user to provide via said interface analysis information regarding said future care to allow informed choices of said electives to be made;
   receiving from said input user via said interface at least one election of at least one of said electives;
   storing in a computer-readable registry end-of-life information in a form of an information set corresponding to said participant, said end-of-life information comprising said at least one election;
   upon receiving a request from an output user identifying an occurrence of an incapacitated state in said participant, generating an information product derivative of said information set comprising said participant's election corresponding to said incapacitated state; and
   communicating said information product to an output recipient.

14. The method of claim 13, wherein said analysis information is selected from a group consisting of:
   a. a measurement of an outcome for at least one of said participant's choices regarding care;
   b. a prediction of an outcome for at least one of said participant's choices regarding care;
   c. a comparison of alternative choices regarding said participant's care; and
   d. interaction of drugs identified by participant in said end-of-life information.

15. The method of claim 13, further comprising providing a second input form to said user for subsequent submission, wherein said input form is selected from the group consisting of an executable document and an election form.

16. The method of claim 13, wherein said end-of-life information is selected from the group consisting of:
   a. an end-of-life choice;
   b. an advance directive;
   c. a Do-Not-Resuscitate Order; and
   d. an authorization to donate an organ.

17. The method of claim 16 wherein when said end-of-life information is an end-of-life choice, said end-of-life choice is a choice selected from the group consisting of:
   a. a palliative care choice;
   b. a comfort care choice;

c. a residence choice;
d. a religious choice; and
e. a spiritual choice.

18. The method of claim 16 wherein when said end-of-life information is an advance directive, said advance directive is an advance directive selected from the group consisting of:
   a. a living will;
   b. a medical power of attorney;
   c. a selection of an end-of-life condition response;
   d. a selection of medical treatment; and
   e. a refusal of medical treatment.

19. The method of claim 13, wherein said guidance information comprises:
   a designation of at least one end-of-life condition; and
   a designation of at least one end-of-life condition response, wherein said input user can choose at least one of said at least one end-of-life response for response to at least one of said at least one end-of-life condition.

20. The method of claim 13, wherein said information product is selected from a group consisting of:
   a. an end-of-life choice;
   b. an advance directive;
   c. a Do-Not-Resuscitate Order;
   d. an authorization to donate an organ;
   e. a summary of an information product selected from the group consisting of a through d, above;
   f. a copy of an information product selected from the group consisting of a through e, above; and
   g. a report concerning said end-of-life information.

21. The method of claim 13, wherein said generating step comprises translating said information set into an information product in a language other than that native to said input user.

22. The method of claim 13, wherein said generating step comprises generating an information product legally enforceable in a jurisdiction other than that in which said participant resides.

* * * * *